United States Patent [19]

Jeannette

[11] 4,207,678
[45] Jun. 17, 1980

[54] MULTIPLE DENTAL SHADE GUIDE SYSTEM

[76] Inventor: William W. Jeannette, 28261 Elba, Grosse Ile, Mich. 48138

[21] Appl. No.: 836,488

[22] Filed: Sep. 26, 1977

[51] Int. Cl.² ............................................. A46B 00/00
[52] U.S. Cl. ...................................... 433/203; 433/26
[58] Field of Search ............................................ 32/71

[56] References Cited

U.S. PATENT DOCUMENTS

| 2,805,478 | 9/1957 | Adams | 32/71 |
| 3,507,042 | 4/1970 | Hana | 32/71 |

*Primary Examiner*—Robert Peshock
*Attorney, Agent, or Firm*—Basile and Weintraub

[57] ABSTRACT

A dental shade guide system for increasing the accuracy in matching an artificial tooth coloring to a patient's natural teeth by providing a plurality of primary shade guides, each guide having a specific chroma percentage made from a predetermined formula. Each primary shade guide has a corresponding plurality of secondary shade guides such that each of the corresponding secondary shade guides has a decreased chroma percentage which is determined by varying the value ratio of the primmary shade guide formula. This is accomplished by mixing the primary shade guide formula in varying amounts with a gray or white modifier. In one embodiment of the invention the secondary shade guides provide a chroma range which in selected applications overlaps with the chroma range of several of the primary shade guides providing the practitioner with a more accurate match. A method for making and using the secondary shade guides is disclosed.

4 Claims, 3 Drawing Figures

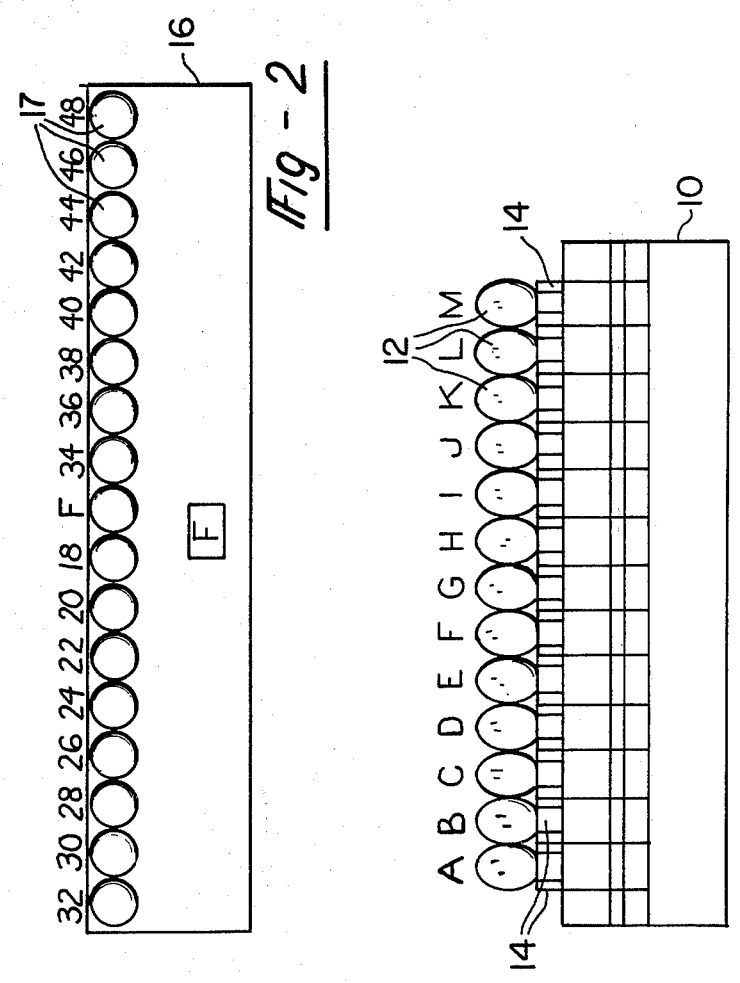

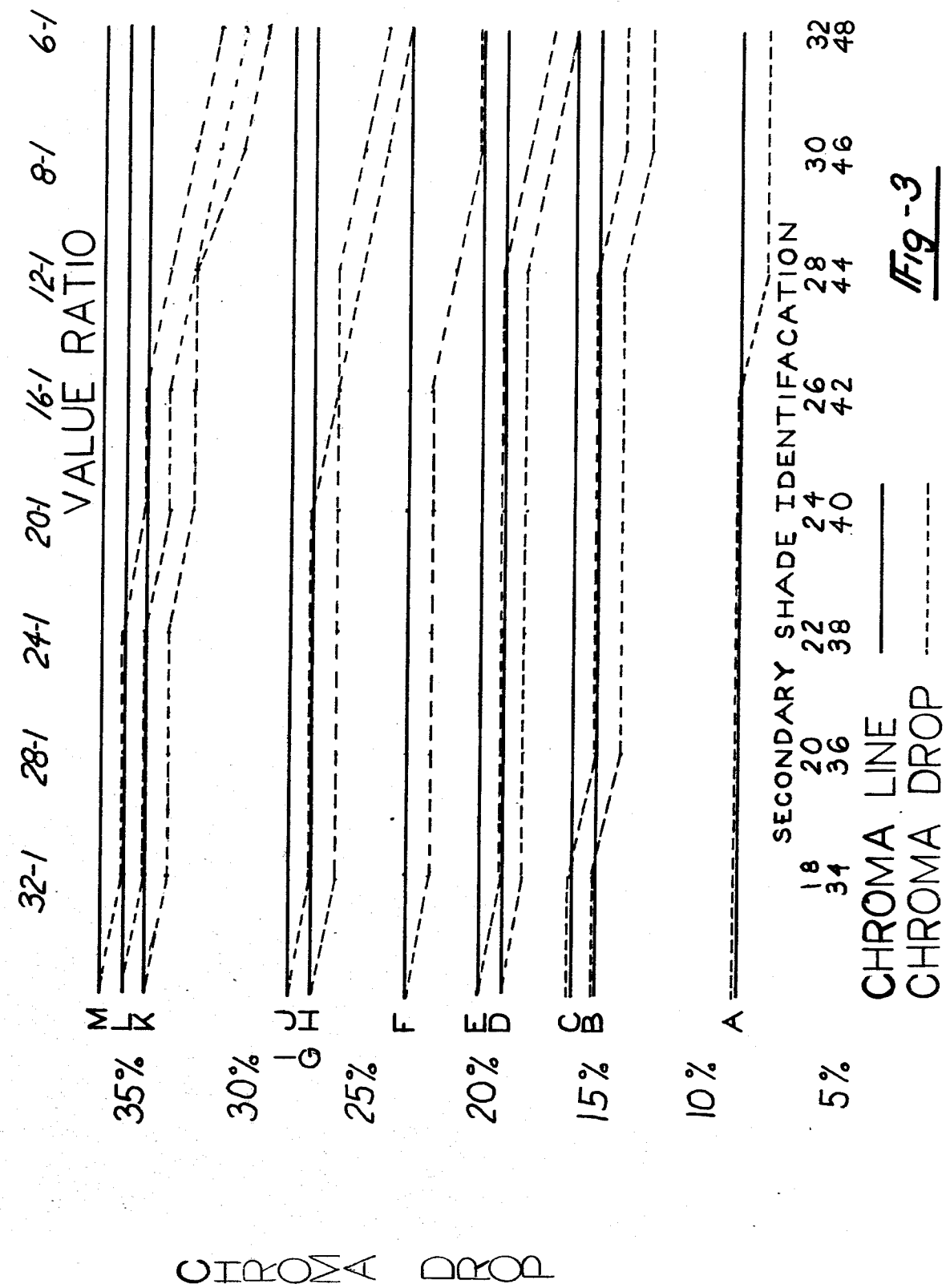

MULTIPLE DENTAL SHADE GUIDE SYSTEM

BACKGROUND OF THE INVENTION

I. Field of the Invention

The present invention generally relates to dental shade guides and, more particularly, to a dental shade guide system for accurately matching an artificial tooth coloring to a patient's natural teeth.

II. Description of the Prior Art

Dental shade guides serve a very useful purpose in assisting a dentist in selecting the proper shade for an artificial tooth in making a dental restoration. In assisting him to select the proper shade of material, the dentist employs a shade guide carrying a number of artificial teeth of the various shades available, the procedure being that the dentist places the shade guide teeth in front of the patient's natural teeth to select a shade most closely approximating the coloring of the patient's natural teeth. Shade guides, as heretofore known, have a number of shortcomings in that they are not normally adapted to insure an accurate color matching because of the considerable color variations of natural teeth.

The progress of restorative dentistry can be easily measured by the growing public awareness of its existence as patients are no longer satisfied with dental restoration of merely restoring the function of the lost tooth. The patient now insists that the artificial tooth have a vital and natural appearance; but, for the reasons aforementioned, the area of tooth color matching is impeded due to the lack of availability of a large number of dental shades covering a wide range of colors. The area of tooth color matching also lacks a simple and accurate method for manufacturing such shades.

Known prior art examples of tooth shade guides are disclosed in U.S. Pat. Nos. 537,553; 825,578; and 2,479,543. These patents disclose various dental shade guides which are relevant to applicant's invention. Each of these dental shade guides has deficiencies of the type aforementioned in that they do not enable a dentist to readily compare artificial teeth of varying shades with the patient's natural teeth to enable a dentist to select an artificial tooth which will match the natural teeth with a substantial degree of accuracy.

III. Prior Art Statement

In the opinion of the applicant, the aforementioned prior art constitutes the closest prior art of which the applicant is aware.

SUMMARY OF THE INVENTION

The present invention, which will be described subsequently in greater detail, comprises a dental shade guide system having a first shade guide holder including a plurality of primary shade guides mounted thereon. Each of the primary shade guides has a specific chroma percentage differing from the other primary shade guides, the total number of primary shade guides covering a wide chroma range. A plurality of second holders are provided, each holder having a plurality of secondary shade guides mounted thereon. The secondary shade guides in each holder correspond to one of the primary shade guides such that each secondary shade guide has a chroma percentage which is determined by varying the value ratio of the primary shade guide. This is accomplished by mixing varying amounts of the formula for the primary shade guide with predetermined amounts of white or gray modifiers.

It is therefore a primary object of the present invention to provide a dental shade guide system which will alleviate the shortcomings of the prior art dental shades in that it will insure an accurate color matching between the natural teeth and the shade guide such that the resulting artificial tooth has a coloring that accurately matches the natural teeth.

It is another object of the present invention to provide a dental shade guide system of the type disclosed herein which will enable a dentist to readily compare the artificial tooth coloring of various shades with the natural teeth in the mouth of a patient and to facilitate the selection of an artificial tooth to match the natural teeth adjacent to which the artificial tooth is to be located, all of which is accomplished in a simple and economical manner.

Other objects, advantages and applications of the present invention will become apparent to those skilled in the art of dental shade guide systems when the accompanying description of one example of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 1 is a plan front view of a primary dental shade guide holder forming one element of the inventive system and incorporating the principles of the present invention;

FIG. 2 is a plan front view of a secondary dental shade guide holder incorporating applicant's inventive system; and FIG. 3 is a graphic illustration of the chroma relationship between the primary and secondary dental shade guides utilized in applicant's inventive dental shade guide system.

DESCRIPTION OF THE PREFERRED EMBODIMENT

Referring now to the drawings and, in particular, to FIG. 1 wherein there is illustrated one example of the present invention in the form of a primary dental shade holder 10 having a plurality of primary dental shade guides 12 in the form of artificial teeth. Individual shade guides 12 may be made of a plurality of materials, such as plastic or the like, and are connected to the holder 10 by any suitable means, such as removable shanks 14. As aforementioned, the head of each shade guide 12 is shaped to simulate a natural tooth and facilitates the use of the shade guide in the conventional manner. The shade guides 12 are so constructed that the dentist merely positions one of the shade guides 12 adjacent the natural tooth to obtain a comparison between the natural tooth and the artificial tooth or shade guide 12. This selection is made by the dentist's utilizing the primary dental shade guides 12 until one of the primary dental shade guides 12 is established as being closest in color to the natural tooth. The dentist then utilizes one of a plurality of secondary dental shade guide holders 16 to complete the selection. One example of a secondary dental shade guide 16 is illustrated in FIG. 2 of the drawings and will be described in greater detail hereinafter.

In seeking to make an exact color match, it is normally necessary to evaluate the three characteristics of any colored objects. These characteristics are hue, chroma and value. The hue, as is well known, is a color or the name of a color, for example, red, blue, orange, green, violet, and so forth. A hue may be a primary color or the result of a combination of colors. The chroma is often described as the amount of saturation or strength of the hue. For example, a certain red and a certain pink may have a certain hue; however, the red may have a stronger saturation of hue and therefore a higher chroma. The pink is really a diluted red and, thus, has a low chroma. Value is the relative amount of the white or gray in the hue. Value is one of the most important factors in proper tooth matching, as a tooth of high value is generally bright and vital in appearance, while a tooth of low value will generally have a gray or non-vital appearance. It is generally a customary practice in the provision of dental shade guides to provide dental shade holders and shades, such as that illustrated in FIG. 1, wherein the dental shade guides 12 have hues that vary slightly from tooth to tooth, whereas the chroma varies a very substantial amount. It should be noted that all of the shade guides on a particular shade guide holder generally have different value levels. For example, thirteen shade guides designated "A" through "M" in FIG. 1 are shown in the graph (FIG. 3) in accordance with their difference in chroma; that is, the percentage of chroma drop. The dental shade guide "A" has the lowest chroma percentage, while the shade guide "M" has the highest chroma percentage. As seen in FIG. 3, the primary shade guides "A" through "M" are designated by a solid horizontal line extending across the face of the chart; however, it should be understood that the value ratio of the various primary shade guides "A" through "M" is not actually changed but is illustrated as a horizontal line across the chart for purposes which will be described hereinafter. It should suffice to say that the horizontal lines indicative of the chroma percentage of the shade guides "A" through "M" facilitate the dentist in determining which shade guide is the most appropriate shade guide to use in the selection of a color for the artificial tooth.

The actual percentage for the chroma drop for the shade guides "A" through "M" and the actual percentage of the chroma drop for the secondary shade guides are determined from conventionally available information, the following chart being illustrative of one example. It should be understood that applicant's invention has applicability to numerous, conventionally available shades and shade modifiers, all of which will be explained hereinafter.

The following formulations are for shade guides manufactured by Ceramco Equipment Corporation of New York:

| SHADE FORMULATIONS | | | | | |
|---|---|---|---|---|---|
| | PERCENT OF COLOR | | | | |
| SHADE | WHITE | PINK | YELLOW | ORANGE | GREY |
| A | 90.88 | | 4.08 | 5.04 | |
| B | 83.47 | 7.12 | 7.63 | | 1.78 |
| C | 82.44 | 8.03 | 8.03 | | 1.50 |
| D | 78.72 | 4.23 | 7.07 | 8.39 | 1.59 |
| E | 78.54 | 8.13 | 12.19 | | 1.14 |
| F | 75.75 | 8.89 | 11.43 | 2.51 | 1.42 |
| G | 73.37 | 2.67 | 13.37 | 10.59 | |
| H | 68.70 | 12.09 | 15.36 | | 3.85 |
| I | 70.82 | 14.05 | 13.27 | .77 | 1.09 |
| J | 70.75 | 10.87 | 13.77 | 2.87 | 2.04 |
| K | 63.84 | 5.07 | 11.84 | 16.75 | 2.50 |
| L | 63.70 | 12.84 | 14.87 | 6.69 | 1.90 |
| M | 59.77 | 4.06 | 16.23 | 16.07 | 2.28 |

It should be noted that the inventive shade guide system utilized to drop the chroma is used in conjunction with a porcelain material. The porcelain material is then baked on either a precious or non-precious metal.

Each of the secondary dental shade guide holders 16 (only one of which is shown in FIG. 2) comprises a plurality of shade guides 17 which correspond to one of the primary dental shade guides 12 and wherein each secondary shade guide 17 corresponds to that one primary shade having a formulation which has been modified by a predetermined amount. For example, the formulation in the shade "F" has a chroma value of approximately 23 percent in its commercially available state. The formulation is commercially available in powder form.

FIG. 2 illustrates the secondary shade holder 16 that corresponds to the primary shade guide "F." Accordingly, the guide "F" is mounted in the center of the secondary shade guide 16. The secondary shade guides 18 to 32 mounted to the left of the primary shade guide "F" represent shade guides having a primary formulation that has been varied by the addition of a white modifier, while the shade guides 34 to 48 mounted to the right of the primary shade guide "F" represent shade guides having a primary formulation that has been varied by the addition of a gray modifier.

The formulation for the secondary shade guides 18 through 32 is obtained by mixing a proportion of the formulation of the primary shade guides in powder form by weight to the powder form by weight of the white modifier. The formulation in the secondary shade guides 34 to 48 is obtained by mixing the formulations of the primary shade guide by weight in powder form to the gray modifier in powder form. The shade 18 is made by mixing one part modifier to 32 parts of the powder formulation that is used to manufacture the shade "F"; the shade 20 has one part white modifier to 28 parts of "F" formulation; the shade 22 has a value ratio of 24 to 1; the shade 24 has a value ratio 20 to 1; the shade 26 has a value ratio of 16 to 1; the shade 28 has a value ratio of 12 to 1; the shade 30 has a value ratio of 8 to 1; while the shade 32 has a value ratio of 6 to 1; that is, 6 parts of "F" formulation to 1 part white modifier. Similarly, the shades 34 through 48 have the same ratios utilizing a gray modifier instead of a white modifier, the shade 34 having a 32 to 1 ratio and the subsequent shades 36 through 48 having the aforementioned ratios respectively 28 to 1 through 6 to 1.

The chroma drop for the shade "F" when a modifier (whether it be white or gray) is added in the aforementioned manner, as illustrated in FIG. 3 of the drawings. By maintaining the horizontal line indicative of the basic shade "F", relative change in the chroma drop can be seen between the modified and unmodified shades. It should be understood that for each primary shade "A" through "M" there is provided a secondary shade guide holder 16, each having preferably 16 secondary shades with value ratios that have been determined in the aforementioned manner. For each of the shade guides "A" through "M" there is provided in FIG. 3 a graph which illustrates the percentage of chroma drop for each primary shade as it is modified in accordance with the aforementioned value ratios. It can be seen that the horizontal chroma lines of the primary shades "A" through "M" will intersect with and have the same chroma percentage as other shades which have been modified, providing the dentist with a choice as to the appropriate shade which may be utilized to provide a patient with an artificial tooth having a coloring most accurately matching the patient's natural teeth.

It can thus be seen that applicant has provided a new and improved dental shade guide system. It should also be understood that other forms of the invention may be had, all coming within the spirit of the invention and scope of the appended claims.

What is claimed is as follows:

1. A method for selecting a coloration for artificial teeth to match exactly that of a patient's natural teeth comprising the steps of:
   (a) comparing the patient's natural teeth with a plurality of primary shade guides, deployed upon a first shade guide holder, each primary shade guide having a specific chroma percentage and each primary shade guide having a different chroma percentage than the other shade guides such that the shade guides cover a specific chroma range;
   (b) selecting the primary shade guide which matches most closely the patient's natural teeth;
   (c) from a plurality of secondary shade guide holders, each secondary shade guide holder corresponding to one of said primary shade guides and having a plurality of secondary shade guides provided thereon, selecting the secondary shade guide holder corresponding to the primary shade guide selected in step b;
   (d) comparing the patient's natural teeth with the secondary shade guides provided on the secondary shade guide holder selected in step c, each said secondary shade guide having a chroma percentage which is defined by a pre-determined value ratio with respect to the chroma percentage of the corresponding primary shade guide, achieved by the addition of a value modifier to the coloring formulation for said primary shade guide in pre-determined proportion specified for each such secondary shade guide; and
   (e) selecting the secondary shade guide which matches most closely the coloration of the patient's natural teeth.

2. The process of claim 1 wherein the patient's natural teeth are compared with primary and secondary shade guides in the form of simulated teeth.

3. The process of claim 1 wherein colorations for artificial teeth, corresponding to a selected number of said secondary shade guides, are fabricated by mixing, in accordance with the specified ratios, the coloring formulation for its corresponding primary shade guide with a white modifier.

4. The process of claim 1 wherein colorations for artificial teeth, corresponding to a selected number of said secondary shade guides, are fabricated by mixing, in accordance with the specified ratios, the coloring formulation for its corresponding primary shade guide with a white modifier.

* * * * *